United States Patent
Moses et al.

(10) Patent No.: US 11,504,533 B2
(45) Date of Patent: Nov. 22, 2022

(54) COMPACT HEARING AIDS

(71) Applicant: NANOEAR CORPORATION, INC., Houston, TX (US)

(72) Inventors: Ron L. Moses, Bellaire, TX (US); Michael M. Moore, Miami Beach, FL (US); Christopher Salthouse, Bellaire, TX (US)

(73) Assignee: NANOEAR CORPORATION, INC., Houston, TX (US)

( * ) Notice: Subject to any disclaimer, the term of this patent is extended or adjusted under 35 U.S.C. 154(b) by 0 days.

(21) Appl. No.: 17/354,020

(22) Filed: Jun. 22, 2021

(65) Prior Publication Data
US 2021/0308461 A1    Oct. 7, 2021

Related U.S. Application Data

(63) Continuation of application No. 16/593,070, filed on Oct. 4, 2019, now Pat. No. 11,083,891.
(Continued)

(51) Int. Cl.
*A61N 1/36* (2006.01)
*H04R 25/00* (2006.01)
*A61N 1/378* (2006.01)

(52) U.S. Cl.
CPC ......... *A61N 1/36036* (2017.08); *A61N 1/378* (2013.01); *H04R 25/602* (2013.01);
(Continued)

(58) Field of Classification Search
CPC .. A61N 1/36036; A61N 1/378; H04R 25/602; H04R 25/604; H04R 25/606; H04R 25/65; H04R 2225/67
(Continued)

(56) References Cited

U.S. PATENT DOCUMENTS

| 5,176,620 A | 1/1993 | Gilman |
| 5,220,918 A | 6/1993 | Heide et al. |

(Continued)

FOREIGN PATENT DOCUMENTS

| EP | 3864861 A1 | 8/2021 |
| EP | 3864863 A1 | 8/2021 |

(Continued)

OTHER PUBLICATIONS

International Search Report and Written Opinion dated Jan. 20, 2020 for Application No. PCT/US2019/054750.
(Continued)

*Primary Examiner* — Sean H Nguyen
(74) *Attorney, Agent, or Firm* — Patterson + Sheridan, LLP

(57) ABSTRACT

The present disclosure relates to compact hearing aids, components thereof, and support systems therefor, as well as methods of insertion and removal thereof. The compact hearing aids generally include a sensor, such as a microphone, an actuation mass, an energy source for providing power to the compact hearing aid, a processor, and an actuator enclosed in a housing that is designed to be inserted through the tympanic membrane during a minimally-invasive outpatient procedure. In operation, the microphone receives sound waves and converts the sound waves into electrical signals. A processor then modifies the electrical signals and provides the electrical signals to the actuator. The actuator converts the electrical signals into mechanical motion, which actuates the actuation mass to modulate the velocity or the position of the tympanic membrane.

20 Claims, 15 Drawing Sheets

Related U.S. Application Data

(60) Provisional application No. 62/742,525, filed on Oct. 8, 2018.

(52) U.S. Cl.
CPC ......... *H04R 25/604* (2013.01); *H04R 25/606* (2013.01); *H04R 25/65* (2013.01); *H04R 2225/67* (2013.01)

(58) Field of Classification Search
USPC ........................................................ 381/322
See application file for complete search history.

(56) References Cited

U.S. PATENT DOCUMENTS

| | | |
|---|---|---|
| 5,338,287 A | 8/1994 | Miller et al. |
| 5,772,575 A | 6/1998 | Lesinski et al. |
| 5,914,507 A | 6/1999 | Polla et al. |
| 6,068,589 A | 5/2000 | Neukermans |
| 6,084,975 A | 7/2000 | Perkins |
| 6,137,889 A | 10/2000 | Shennib et al. |
| 6,387,039 B1 | 5/2002 | Moses |
| 7,748,493 B2 | 7/2010 | Moses et al. |
| 7,983,435 B2 | 7/2011 | Moses |
| 8,401,214 B2 | 3/2013 | Perkins et al. |
| 8,433,083 B2 | 4/2013 | Abolfathi et al. |
| 8,630,712 B2 | 1/2014 | Moses et al. |
| 11,083,891 B2 | 8/2021 | Moses et al. |
| 11,223,913 B2 | 1/2022 | Moore et al. |
| 2003/0065245 A1 | 4/2003 | Easter et al. |
| 2007/0154030 A1 | 7/2007 | Moses |
| 2008/0255406 A1 | 10/2008 | Ball et al. |
| 2009/0010462 A1 | 1/2009 | Ekchian et al. |
| 2009/0281367 A1 | 11/2009 | Cho et al. |
| 2012/0014546 A1 | 1/2012 | Pura et al. |
| 2013/0261701 A1 | 10/2013 | Kuratle et al. |
| 2015/0382117 A1 | 12/2015 | Vermeiren |
| 2016/0100263 A1 | 4/2016 | Huettenbrink |
| 2017/0208403 A1 | 7/2017 | Nakajima |
| 2018/0160242 A1 | 6/2018 | Sriskandarajah |
| 2018/0169410 A1 | 6/2018 | Leigh et al. |
| 2020/0108249 A1 | 4/2020 | Moses et al. |
| 2021/0051421 A1 | 2/2021 | Moore et al. |

FOREIGN PATENT DOCUMENTS

| | | |
|---|---|---|
| KR | 20070093049 A | 9/2007 |
| KR | 20100005940 A | 1/2010 |
| KR | 100999690 B1 | 12/2010 |
| WO | 2010033932 A1 | 3/2010 |
| WO | 10/133704 A2 | 11/2010 |
| WO | 2010133704 A3 | 6/2011 |
| WO | 2020076640 A1 | 4/2020 |

OTHER PUBLICATIONS

International Search Report and Written Opinion dated Jan. 31, 2020 for Application No. PCT/US2019/054739.
Extended European Search Report dated Jun. 15, 2022 for Application No. 19872066.6.
First Examination Report dated Feb. 14, 2022 for Application No. 202117019178.
First Examination Report dated Feb. 16, 2022 for Application No. 202117019385.
International Search Report and Written Opinion dated Apr. 18, 2022 for Application No. PCT/US2021/054469.
Examination Report dated Apr. 11, 2022 for Application No. 3,115,578.

COMPACT HEARING AIDS

CROSS-REFERENCE TO RELATED APPLICATIONS

This application is a continuation of U.S. patent application Ser. No. 16/593,070, filed Oct. 4, 2019, which claims benefit of U.S. Provisional Patent Application Ser. No. 62/742,525, filed on Oct. 8, 2018, each of which is herein incorporated by reference in its entirety.

BACKGROUND

Field

Embodiments of the present disclosure generally relate to assistive hearing devices and methods of implantation thereof. More particularly, embodiments of the present disclosure are related to compact hearing aids mounted internally into an ear canal, for example, into or across the tympanic membrane, which provide vibration transduction to modulate the velocity or the position of the tympanic membrane.

Description of the Related Art

Hearing aids are well known and typically include a microphone, an amplifier, and a speaker. Typically, the microphone receives a sound wave and converts the wave into an electrical signal, the amplifier amplifies the electrical signal, and the speaker converts the amplified signal into amplified sound waves that impart vibrations to the tympanic membrane or ear drum in the ear. Traditionally, hearing aids are mounted outside the ear canal, particularly around the outer ear. The externally mounted hearing aid has the advantage of accessibility to change batteries and to adjust the volume of sound. However, many users find such externally mounted hearing aids to be relatively bulky and objectionable for cosmetic and comfort reasons.

An alternative to externally mounted hearing aids are internally mounted hearing aids disposed in an ear canal of a user. Conventional internally mounted hearing aids offer better cosmetic appearance, but have disadvantages as well. For instance, the typical internally mounted hearing aid blocks the majority, if not all, of the ear canal diameter. Such blockage can cause the body of the user to produce an excessive amount of ear wax in the ear canal and can cause ear infections. Further, the blocking of the ear canal obstructs the natural transmission of sound waves through the ear canal and negatively impacts the hearing quality. Unless a user is totally hearing impaired, any ability of the tympanic membrane to register the natural occurring sound waves is reduced or eliminated. Thus, the user is substantially dependent upon the sound fidelity of the hearing aid. Still further, the typical internally mounted hearing aids may still be somewhat visible in the ear canal.

Some hearing systems deliver audio information to the ear through electromagnetic transducers. A microphone and amplifier transmit an electronic signal to a transducer that converts the electronic signal into vibrations. The vibrations vibrate the tympanic membrane or parts of the middle ear that transmit the sound impulses without reconverting to audio sound waves. Historically, a separate magnet, or any suitable actuator, was remotely mounted at or near the tympanic membrane. The interaction between the magnetic fields of the transducer receiving the electronic signal and the magnet mounted at or near the tympanic membrane causes the magnet to vibrate and thus mechanically transmits the sound through the vibration to the ear at the cochlea. Typically, however, the remainder of the hearing aid is inserted into the ear canal or on the outer ear and can cause the problems discussed above. Still further, the transducers and/or magnets of the hearing aids are mounted in a relatively invasive procedure. For instance, one contact transducer having a magnet is installed by drilling through the mastoid bone, cutting through the tympanic membrane, microscopically drilling a bone structure, and screwing the magnet to any one or more of the middle ear bones. Such procedures are often painful and expensive, and can have serious complications.

As described above, there are various types of hearing aids that are used to amplify and transmit sound waves to the hearing center of the brain resulting in the perception of sound. However, conventional hearing aids do not selectively suppress sound waves generated by background noise and excessively loud noises while simultaneously transmitting normal speech and other desirable acoustic signals. Noise suppression could be used by astronauts on long duration missions such as the International Space Station or a Mars mission that want to selectively suppress background noise created by rotating machinery, air handling systems, and environmental control systems while still allowing the astronaut to hear the sound waves generated by other astronauts and other desirable acoustic signals. Amplification of selective frequencies could be used in a military operation, wherein sound waves generated by enemy combatants could be amplified and sent to the hearing center of the brain while all other sound waves are transmitted in a normal manner. Additionally, the traditional types of hearing aids do not allow a user to receive signals or sound waves that are not audible to a normal person, such as in covert communication.

Therefore, there is a need in the art for improved hearing aids, which can be inserted in the ear canal and/or through the tympanic membrane using minimally-invasive surgical procedures.

SUMMARY

The present disclosure relates to compact hearing aids, components thereof, and support systems therefor, as well as methods of insertion and removal thereof. The compact hearing aids generally include a sensor, such as a microphone, an actuation mass, an energy source for providing power to the compact hearing aid, a processor, and an actuator enclosed in a housing that is designed to be inserted through the tympanic membrane during a minimally-invasive outpatient procedure. In operation, the microphone receives sound waves and converts the sound waves into electrical signals. A processor then modifies the electrical signals and provides the electrical signals to the actuator. The actuator converts the electrical signals into mechanical motion, which actuates the actuation mass to create inertia internal to the housing, and the housing is configured to modulate the velocity or the position of the tympanic membrane.

In one embodiment, a tympanic membrane actuation assembly is disclosed. The tympanic membrane actuation assembly includes at least one mass configured to be disposed on at least one of a medial side or a lateral side of a tympanic membrane of a user, and at least one actuator coupled to the mass and configured to be disposed on at least one of a medial side or a lateral side of the tympanic membrane or through the tympanic membrane of a user, the actuator being configured to convert electrical signals into mechanical motion to move the mass and modulate the tympanic membrane.

In another embodiment, a hearing aid, which is insertable through a user's tympanic membrane to amplify certain frequencies and cancel other frequencies, is disclosed. The hearing aid includes a tympanic membrane actuation assembly, which includes at least one mass configured to be disposed on at least one of a medial side or a lateral side of the tympanic membrane of a user, and at least one actuator coupled to the mass and configured to be disposed on at least one of a medial side or a lateral side of the tympanic membrane or through the tympanic membrane of a user, the actuator being configured to convert electrical signals into mechanical motion to move the mass and modulate the user's tympanic membrane.

In yet another embodiment, a hearing aid, which is insertable through a user's tympanic membrane to amplify certain frequencies and cancel other frequencies, is disclosed. The hearing aid includes a housing having a first flange and a second flange having a groove therebetween, the housing encloses a microphone, a processor coupled to the microphone, and a tympanic membrane actuation assembly, which includes a mass, the mass having a first battery disposed in the first flange, and a second battery disposed in the second flange, the first battery being configured for placement on a lateral side of the tympanic membrane, the second battery being configured for placement on a medial side of the tympanic membrane, a connecting member coupling the first battery to the second battery, the connecting member being configured for placement through the tympanic membrane, and an actuator coupled to the mass and disposed within the connecting member, the actuator being configured to convert electrical signals into mechanical motion to move the mass and modulate the user's tympanic membrane.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope. The disclosure may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure relates to compact hearing aids, components thereof, and support systems therefor, as well as methods of insertion and removal thereof. The compact hearing aids generally include a sensor, such as a microphone, an actuation mass, an energy source for providing power to the compact hearing aid, a processor, and an actuator enclosed in a housing that is designed to be inserted through the tympanic membrane during a minimally-invasive outpatient procedure. In operation, the microphone receives sound waves and converts the sound waves into electrical signals. A processor then modifies the electrical signals and provides the electrical signals to the actuator. The actuator converts the electrical signals into mechanical motion, which actuates the actuation mass to modulate the velocity or the position of the tympanic membrane.

The Anatomy of the Ear

Figure 1:
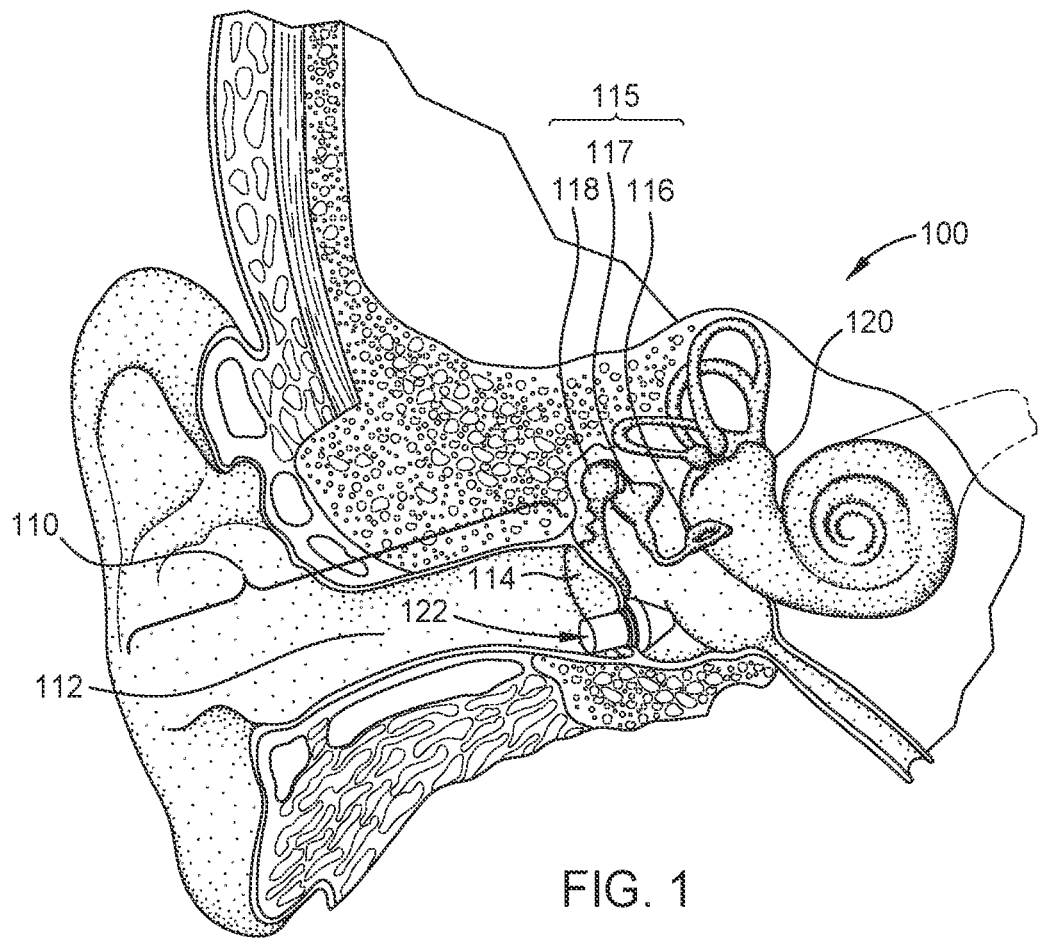
FIG. 1 is a cross-sectional schematic view of the anatomy of an ear having a hearing aid inserted through the tympanic membrane thereof.

FIG. 1 is a cross-sectional schematic view of the anatomy of an ear 100 having a hearing aid inserted through the tympanic membrane thereof. The ear includes an outer ear 110, an ear canal 112 coupled to the outer ear 110, a tympanic membrane 114 disposed near a proximal end of the ear canal 112 from the outer ear 110. The structure of the outer ear 110 provides a "funnel" to direct and amplify the amplitude of the sound waves into the ear canal 112. An ossicular chain 115, located in a middle ear and disposed on a medial side of the tympanic membrane 114 from the outer ear 110, couples and amplifies vibrations from the tympanic membrane 114 to an inner ear having a spiral structure known as the cochlea 120. The cochlea 120 converts the vibrations into impulses to the brain.

Hearing aids, such as hearing aid 122, of the present disclosure can be inserted through the outer ear 110 into the ear canal 112 and at least partially through the tympanic membrane 114. The hearing aid 122 generally includes a sensor, such as a microphone, and at least one eardrum stimulating member described in more detail below. The hearing aid 122 generally receives sound waves conducted from the outer ear 110 through the ear canal 112, converts the sound waves into electrical or electromagnetic signals, and converts the electrical signals into mechanical motion, which is typically called a feed-forward system. The mechanical motion is used to impact the tympanic membrane 114, and/or portions of the middle and inner ear, to vibrate the ossicular chain 115, specifically the malleus 118, the incus 117, and the stapes 116. These three bones in the ossicular chain 115 act as a set of levers that amplify the amplitude of the vibrations received by the tympanic membrane 114. The stapes 117 is coupled to the entrance of a spiral structure known as the cochlea 120 that contains an inner ear fluid. The mechanical vibrations of stapes 117 cause the fluid to develop fluid impulses that cause small hair-like cells (not shown) in the cochlea 120 to vibrate. The vibrations are transformed into electrical impulses, which are transmitted to neuro-pathways in the hearing center of the brain resulting in the perception of sound.

Figure 2:
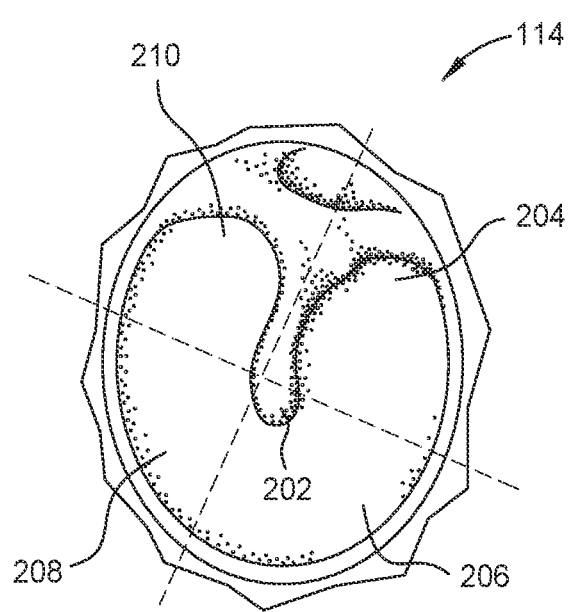
FIG. 2 is a schematic plan view of a right tympanic membrane.

FIG. 2 is a schematic plan view of the tympanic membrane 114 (a right tympanic membrane is shown as an example). The tympanic membrane 114 is generally an oval shape, which is slightly drawn inwards at its center, called the umbo 202, which is where the handle of malleus (shown in FIG. 1 and described above) is attached. The tympanic membrane is conceptually divided into four quadrants: the anterior superior quadrant 204, the anterior inferior quadrant 206, the posterior inferior quadrant 208, and the posterior superior quadrant 210.

Compact Hearing Aids and Components Thereof

The present disclosure relates to compact hearings aids, components thereof, and support systems therefore. The embodiments described herein provide exemplary configurations of compact hearing aids contemplated by the present disclosure. However, any other suitable configurations for hearing aids that modulate the velocity or the position of the tympanic membrane, by direct or indirect modulation, are also contemplated. The embodiments that follow discuss inserting the disclosed compact hearing aids through the tympanic membrane, as an example; however, the compact hearing aids are also disposable in other locations within the ear.

Figure 3:
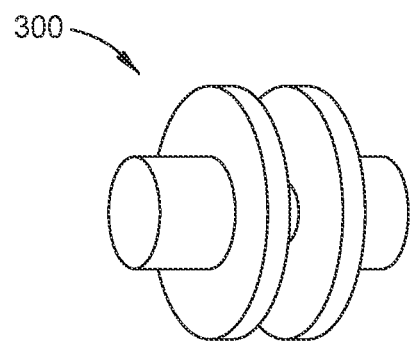
FIG. 3 is schematic perspective view of a compact hearing aid.
Figure 4:
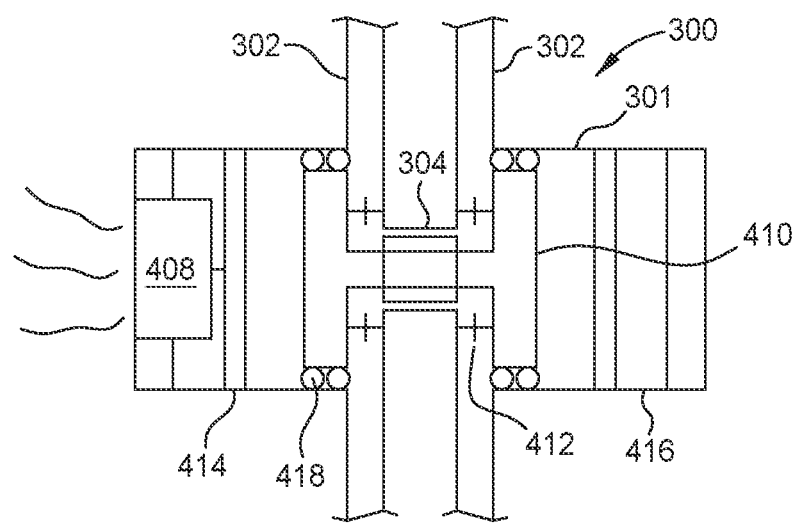
FIG. 4 is a cross-sectional view of the compact hearing aid of FIG. 3.

FIG. 3 is a schematic perspective view of a compact hearing aid 300. FIG. 4 is a cross-sectional view of the compact hearing aid 300 of FIG. 3. As shown in FIGS. 3 and 4, the compact hearing aid 300 is encompassed in a housing 301, which includes two flange portions 302 coupled by a connecting portion 304. When implanted, the two flange portions 302 are positioned on opposite sides of the tympanic membrane (i.e., one flange portion is in the outer ear and the other portion is in the middle ear) and the connecting portion 304, shown as a narrow tube as an example, transverses the tympanic membrane. The connecting portion 304 is generally positioned along the center axis of the compact hearing aid 300 or parallel to the center axis of the compact hearing aid 300.

As used herein the term flange refers to a portion of the disclosed compact hearing aids, which is lateral or peripheral to a central portion thereof, such as the connecting portion 304.

The one or more flanges and the connecting member generally make up the body of the compact hearing aid. As used herein, the term body generally refers to the one or more flanges and the connecting portion as a unit.

As shown in FIG. 4, the compact hearing aid 300 is enclosed by the housing 301, which houses the various components of the compact hearing aid 300. The various components generally include at least a sensor 408, such as a microphone configured to detect the sound to be processed, a mass which is shown as an energy source 410, an actuator 412 configured to convert electrical signals into mechanical motion, and a processor 414 configured to aid with signal processing and power conversion by modifying electrical signals and transmitting the electrical signals to the at least one actuator, as well as to drive the actuator 412 to move the mass, which is the energy source 410 in this example. Together, the mass and the at least one actuator make up a tympanic membrane actuation assembly. In embodiments in which the energy source 410 is a rechargeable energy source, the compact hearing aid 300 generally also includes a recharging circuit 416.

The sensor 408 is generally fixed within the housing 301 and is configured to receive the sound to be amplified by the compact hearing aid 300 and convert the sound waves or acoustic signals into electrical or electromagnetic signals. The present disclosure contemplates a microphone as the sensor 408 as an example; however, it is contemplated that the sensor 408 is generally any suitable sensor. Suitable sensors include, but are not limited to, high sensitivity microphones, piezoelectric micro-electro-mechanical systems (MEMS) microphones, electrostatic microphones, accelerometers, gyroscopes, and optical sensors. Other suitable sensors include sensors, which may be used to sense otoacoustic emissions (OAEs) or pressures to diagnose ear infections, or other changes in the user or in the performance and device health of the compact hearing aid 300 itself.

While one sensor 408, which is a microphone, is shown as an example, further embodiments of the compact hearing aids described herein include multiple microphones or other sensors, which may be disposed about the lateral aspect of the compact hearing aid, about the medial aspect of the compact hearing aid, or on both the medial and lateral aspects of the compact hearing aid. In yet further embodiments, one microphone, such as sensor 408 is disposed in the compact hearing aid, and one or more other microphones are disposed elsewhere, such as in the ear canal. In such embodiments, the one or more external microphones are directly connected or, or otherwise communicate with, the compact hearing aid 300.

In another embodiment, the sensor 408 may be disposed outside of the housing. In another embodiment, the compact hearing aid 300 may include a second actuator to ensure that the sensor 408 does not move with the housing or the first actuator. In yet another embodiment, the compact hearing aid 300 may further include a passive mechanical coupler to isolate the sensor 408 from the movement of the housing or the first actuator.

The mass is any suitable mass material, component, or combination of components, which may be actuated to modulate the velocity or the position of the tympanic membrane, and may include any suitable number of portions, such as a first portion and a second portion. The mass is generally between about 5 milligrams (mg) and about 40 mg in total. For example, in embodiments comprising a first portion and a second portion, each portion being a battery, the weight is generally between about 10 mg per battery and about 15 mg per battery (totaling between about 20 mg and about 30 mg, respectively).

The energy source 410 is generally any suitable energy source of any suitable configuration, such as a single mass, a thin film battery having multiple, vertically-stacked layers (for example, between 5-20 layers), a radio thermal generator, a super capacitor, a thick film battery, or a traditional lithium (Li) ion battery. As shown in FIG. 4, the mass is the energy source 410, which is dumbbell shaped and disposed centrally within the compact hearing aid 300. In such an embodiment, the energy source 410 itself can be used as the mass to modulate the velocity or the position of the tympanic membrane. In further embodiments, the energy source 410 is disposed medially or laterally within the compact hearing aid and on one side of the tympanic membrane. In yet further embodiments, such as FIGS. 13, 14, 16A-C, 17, and 18, one or more mass portions, such as batteries, are disposed on both the medial and lateral sides of the tympanic membrane and may be connected by a connection member disposed in the housing 301 that traverses the tympanic membrane. In still further embodiments, an energy source and a counter mass, which are connected across the tympanic membrane, are used. The counter mass is generally an inert or inactive mass.

In one embodiment, the diameter of the energy source 410 is less than or equal to 2.5 millimeters (mm) and the height is less than or equal to 1.5 mm. The mass of the energy source 410 is selected to maximize the safety of holding the compact hearing aid in the tympanic membrane and/or based on a passive noise transmission attenuation level, for example less than or equal to 10 decibels (dB). In one embodiment, the mass is generally less than or equal to about 15 milligrams (mg). As described below, the energy source 410 is generally rechargeable. In such embodiments, the charging time is generally less than or equal to about 3 hours and can be charged more than 1,000 times.

The actuator 412 is generally any actuator mechanism, or any plurality of actuator mechanisms, suitable to convert the electrical signals into mechanical motion by moving the mass such that the mass modulates the velocity or the position of the tympanic membrane, and may be disposed on the medial side, the lateral side, both sides of the tympanic membrane, or across the tympanic membrane. The actuator 412 is configured to push the mass, and to retrieve, or pull, the mass, relative to the coupling to the tympanic membrane.

Figure 5:
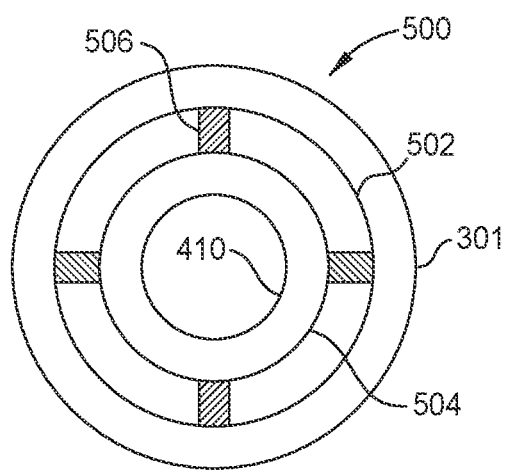
FIG. 5 is a plan view of an actuator.

FIG. 5 is a plan view of an actuator 500 according to one embodiment, which may be used as the actuator 412. The actuator 500 includes at least an outer ring 502 and an inner ring 504, the outer ring 502 being connected to the housing 301 and the inner ring 504 being connected to the mass, such as the energy source 410. The outer ring 502 has a plurality of piezoelectric actuators 506 that can be excited to create the force needed to modulate the inner ring 504 axially and to ultimately modulate the velocity or the position of the tympanic membrane. In another embodiment, the plurality of piezoelectric actuators 506 are individually addressable to provide non-axial modulation of the velocity or the position of the tympanic membrane.

Figure 6:
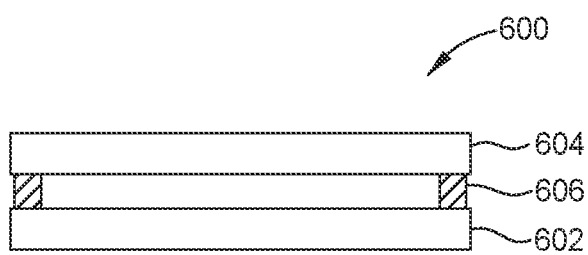
FIG. 6 is a plan view of an alternative embodiment of an actuator.

FIG. 6 is a perspective side view of an actuator 600 according to another embodiment, which may be used as the actuator 412. The actuator 600 includes a first disk 602 and a second disk 604, which are coupled together by a plurality of piezoelectric actuators 606 sandwiched therebetween. At least one of the first disk 602 or the second disk 604 is movable to modulate the velocity or the position of the tympanic membrane. In another embodiment, the plurality of piezoelectric actuators 606 are individually addressable to provide non-axial modulation of the velocity or the position of the tympanic membrane.

Figure 13:
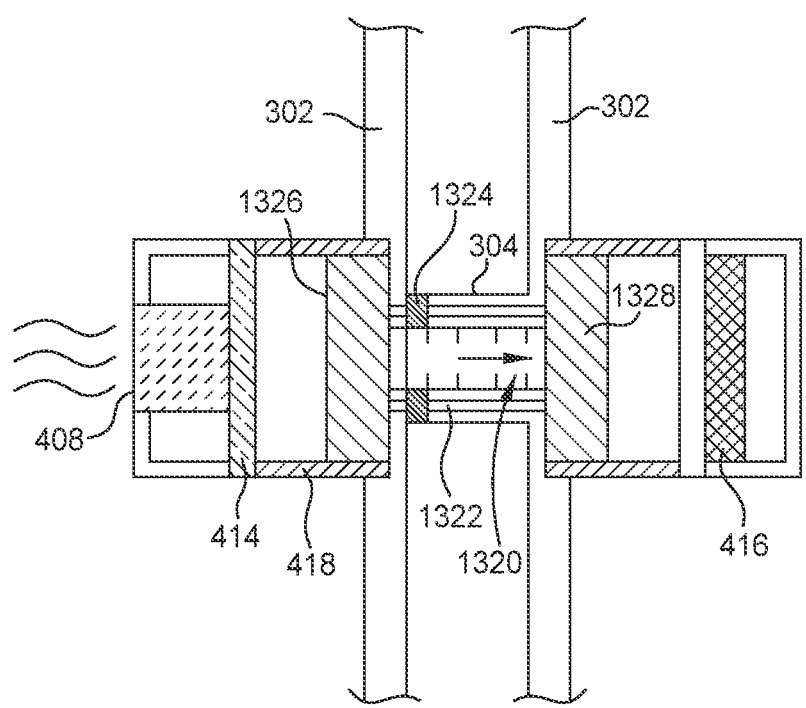
FIG. 13 is a cross-sectional view of a compact hearing aid having an alternative embodiment of an actuator.

FIG. 13 is a cross-sectional view of a compact hearing aid, such as compact hearing aid 300, having an alternative embodiment of an actuator. In the embodiment shown in FIG. 13, the actuator is a piezoelectric stack actuator 1320 that actuates linearly. The base 1324 of the piezoelectric stack actuator 1320 is fixed. As shown, one or more connecting members 1322, shown as disposed around the outside of the piezoelectric stack actuator 1320, connect a first mass 1328 to a trailing mass 1326. The first mass 1328 is displaced by the piezoelectric stack actuator 1320 and the trailing mass 1326 generally follows the movement of the first mass 1328 to move the masses in phase.

Figure 14:
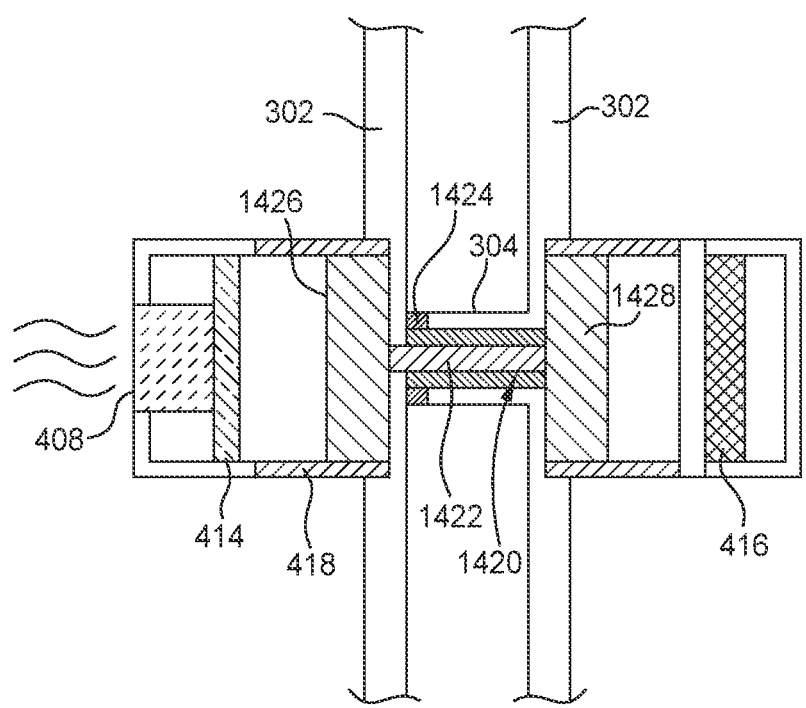
FIG. 14 is a cross-sectional view of a compact hearing aid having an alternative embodiment of an actuator.

FIG. 14 is a cross-sectional view of a compact hearing aid, such as the compact hearing aid 300, having an alternative embodiment of an actuator. In the embodiment shown in FIG. 14, the actuator is a piezoelectric microtube 1420. The base 1424 of the piezoelectric microtube 1420 is fixed. In operation, the piezoelectric microtube 1420 lengthens linearly to displace the first mass 1426. One or more connecting members 1422 connect the first mass 1426 and the second mass 1428. The one or more connecting members 1422 lie in an inner diameter of piezoelectric microtube 1420.

In still further embodiments, the actuator 412 is a linear actuator. For example, the actuator 412 may be a voice coil having a central mass, generally a magnet, with an outer coil wrapped there around, which modulates the force on the mass by energizing the outer coil. Alternatively, the voice coil may be centrally disposed with the magnet disposed therearound. The linear actuator may traverse the tympanic membrane within the compact hearing aid, which when energized, oscillates and creates a modulating force to the tympanic membrane. In another embodiment, the actuator 412 includes a plurality of actuators coupled to the housing 301 and/or the energy source 410. In yet another embodiment, the actuator 412 is a plurality of concentric actuators that create linear movement. In yet another embodiment, the actuator 412 is a rotary actuator that creates a wave that extends radially from the compact hearing aid. In yet another embodiment, the actuator 412 includes a piezo MEMS device or an electrostatic MEMS device with a stepper motor, for example. In yet another embodiment, an actuator may be formed through the combination of two or more of the above-mentioned actuators.

As discussed herein, the disclosed compact hearing aids include one or more actuators. When more than one actuator is used, all of the actuators may be the same type of actuator or more than one type of actuator. When more than one type of actuator is used, the stimulation of the actuators may be in different or similar planes. In one embodiment, the different types of actuators are configured to actuate in different planes at the same time, for example, to grow in length and/or diameter. Additionally, and as discussed further below, the actuator may utilize an impedance matching component, such as a MEMs lever arm depending on the energy and displacement ranges needed to improve the user's hearing.

As shown in FIGS. 4, 13, and 14, the compact hearing aid 300 may also include a movement mechanism 418, such as bearings or a linear slide, which confines the movement of the mass to the direction of the actuation.

The Operation of the Hearing Aid

The processor 414, which is generally an Application Specific Integrated Circuit (ASIC) chip, takes an electrical signal from the sensor 408 that represents the acoustic signals and converts the signals into an electrical signal to drive the actuator 412 and move the mass (e.g., the energy source 410) to modulate the position of the tympanic membrane and thus provide impulses to the user's brain. The mass generally moves a distance of less than or equal to about one millimeter. The direct or indirect modulation of the position of the tympanic membrane improves the hearing of the user.

In addition to converting the signals for modulating the mass, the processor 414 may also bias the sensor 408, and provide safety functions, such as internal temperature and current monitoring.

In some embodiments, the processor 414 encompasses the safety circuitry for the energy source 410, including for appropriately charging and discharging the energy source 410 safely and efficiently.

In even further embodiments, the processor 414 also performs communication functions such that the compact hearing aid can send information to, and receive information from, the external world. For example, the processor 414 generally includes circuitry allowing the compact hearing aid to communicate information about the state of the compact hearing aid, and even the state of the user's ear, to an external recipient.

In even further embodiments, the processor 414 is configured to modify acoustic input to allow for frequency shifting. This frequency shifting processing is useful to optimize the mechanical output, address various frequency responses and transfer functions ultimately to provide the user a superior acoustic experience. For example, certain frequencies or nodes that the device may miss, which have been preidentified, may be captured and shifted so that the user will hear the missed frequency at a different, shifted frequency.

Figure 12:
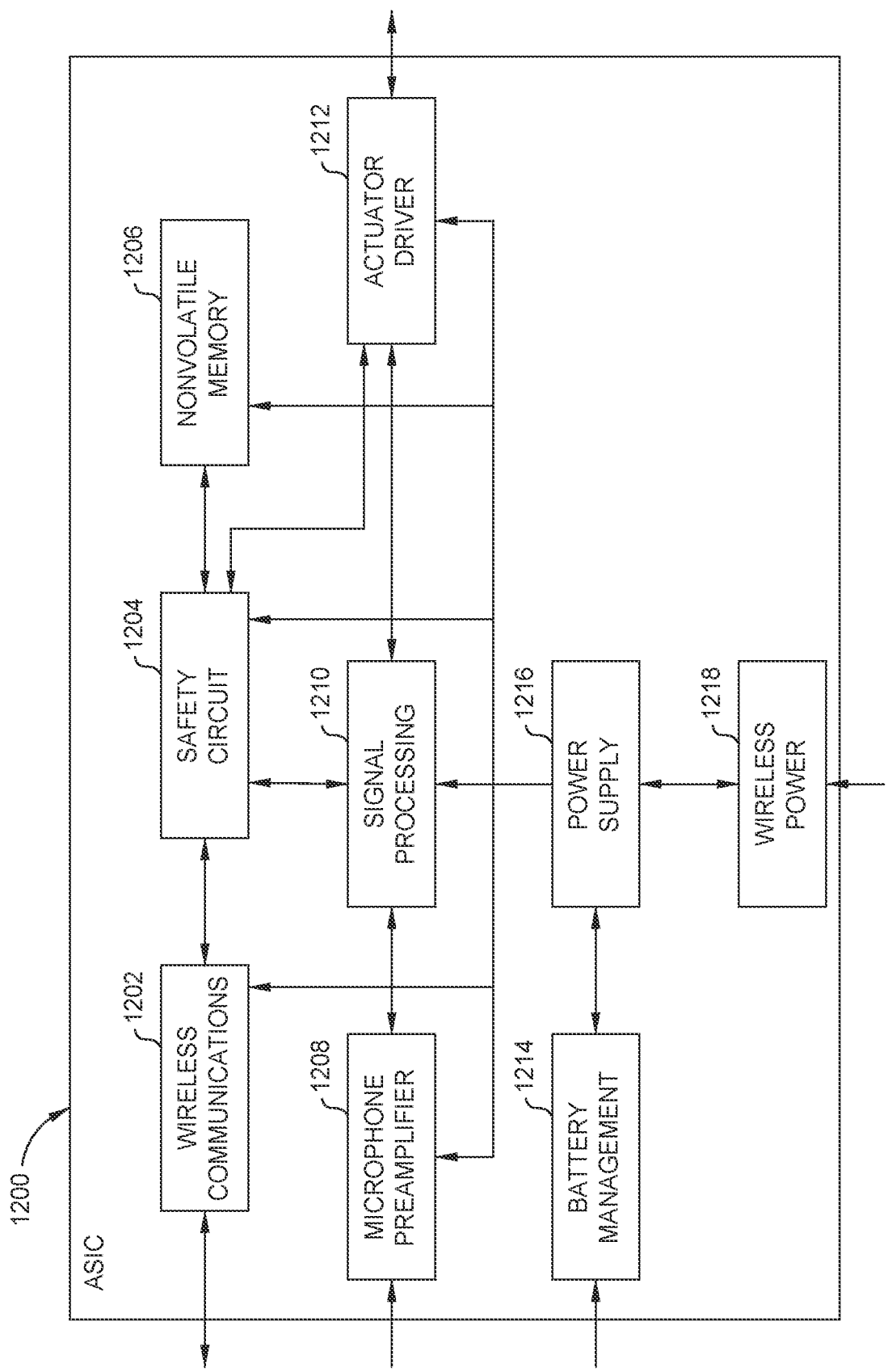
FIG. 12 is a block diagram of an ASIC processor.

FIG. 12 depicts a block diagram of an ASIC processor 1200. The ASIC processor 1200 may be used as the processor 414. The ASIC processor 1200 generally includes a wireless communications component 1202, a safety circuit component 1204, a nonvolatile memory component 1206, a microphone preamplifier component 1208, a signal processing component 1210, an actuator driver component 1212, an energy source management component 1214, a power supply component 1216, and a wireless power component 1218. Wireless communications include, but are not limited to, optical, acoustic, and radio frequency communications.

In one embodiment, the ASIC processor 1200 uses analog signal processing to reduce power needs and minimize digital components. Additionally, the ASIC processor 1200 may be configured to minimize power consumption via programming and/or estimating responses, while maintaining acceptable processing. In another embodiment, the ASIC processor 1200 may be configured to perform frequency communication and/or registration via an audio device, such as a smart phone. For example, the ASIC processor 1200 may be configured to turn the compact hearing aid on and off via an acoustic profile signature. The ASIC processor 1200 may also be configured to change the intensity mode, for example by controlling the amplitude when in uncomfortable acoustic environments, using the acoustic profile signature, to limit amplitude of all frequencies, and/or to provide noise cancellation. Even further, the ASIC processor 1200 may be configured to recognize emergency tones that automatically turn the compact hearing aid on, such as fire alarms, door bells, and glass breaking sounds.

In further embodiments, the ASIC processor 1200 uses digital signal processing.

In another embodiment, the ASIC processor 1200 is wirelessly controlled by radiofrequency (RF) signals. The RF signals may be used to turn the compact hearing aid on and off, to change the intensity mode to control amplitude in uncomfortable acoustic environments, and to provide for tuning and verification tone responses for diagnostics.

The ASIC processor 1200 may also be configured to filter certain frequencies. For example, the disclosed compact hearing aids may further or alternatively include a feedforward system to control feedback by changing frequencies of certain ranges of input to avoid certain resonance frequencies. The disclosed compact hearing aids may also or alternatively include a system with learning algorithms to adjust frequency responses when unique environments produce unique resonance frequencies. OAEs are sounds produced by the inner ear. More specifically, there are hair cells in the inner ear that respond to signals by vibrating. The vibration produces a very quiet sound that reverberates back into the middle ear. It is thought that OAEs help to selectively amplify certain frequencies. Similarly, the compact hearing aids disclosed herein are also configurable to produce a low decibel and patentable frequency signal that will help to amplify the incoming sounds. This extra background sound will help with improving the signal-to-noise (STN) ratio, or it will be uniquely helpful at certain frequencies. This background sound could be a simple single frequency sound, it could be a single complex sound made up of multiple different frequencies, or it could be several sounds, which are fractions of a second apart, or it could generate any of these sounds at specific times depending on the frequency being processed.

The disclosed compact hearing aids are also configurable to self-diagnose by recognizing the OAEs and making adjustments in the device itself to optimize hearing for that particular user.

Additionally, the disclosed compact hearing aids produce an output, to which the inner ear responds and produces a unique OAE, which is correlated with the degree of hearing loss at those frequencies.

Additional Device Components and Configurations

In the embodiment shown in FIG. 4, the compact hearing aid 300 includes a separate recharging circuit 416; however, as discussed above, in other embodiments, much, and sometimes all, of the recharging circuit can be included in the processor 414. The recharging circuit 416 recharges the energy source 410.

In one embodiment, one or more coil arrays for recharging are disposed in or about the flange(s). In another embodiment, one or more coil arrays for recharging are disposed in or about the lateral portion of the compact hearing aid. In yet another embodiment, one or more coil arrays for recharging are disposed in or about the medial portion of the compact hearing aid. In yet another embodiment, one or more coil arrays for recharging are disposed in both the medial and lateral portions of the compact hearing aid. In yet another embodiment, one or more of the coil arrays for recharging may be the same coil that powers the voice coil actuator described above.

Figure 16A:
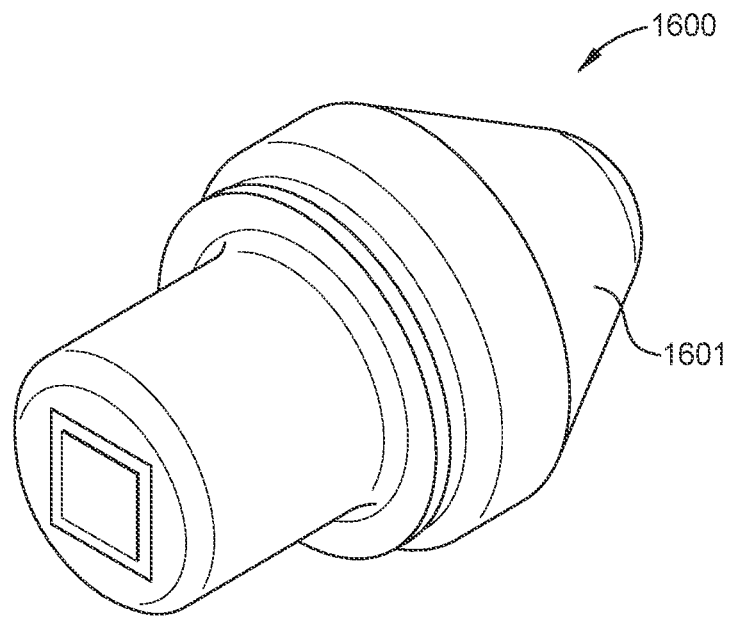
FIGS. 16A-16C depict an alternative embodiment of a compact hearing aid.
Figure 16B:
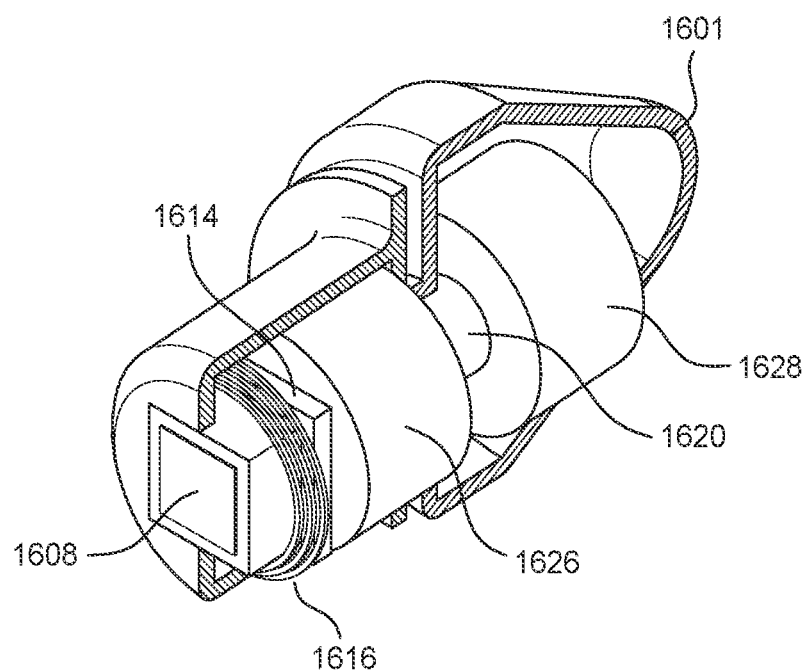
Figure 16C:
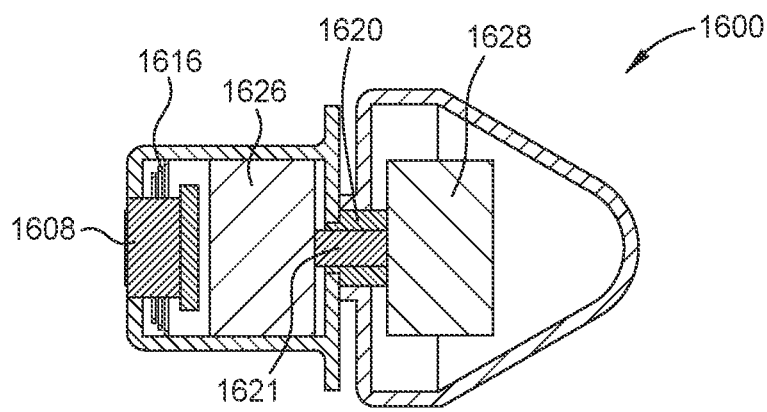

FIGS. 16A-16C depict an alternative embodiment of a compact hearing aid 1600. The compact hearing aid 1600 includes an enclosure housing 1601 that houses at least a microphone 1608, a first mass, shown as a first battery 1626, as an example, a second mass, shown as a second battery 1628, as an example, coupled to the first battery 1626 by a connecting member 1621, and a processor 1614. The connecting member 1621 includes, or is surrounded by, an actuator 1620. The actuator 1620 is generally a tubular or cylindrical stacked piezoelectric actuator having a hole therein to allow the connecting member 1621 to pass therethrough. The height of the actuator 1620 is generally between about 1 mm and about 4 mm, and the outer diameter of the actuator 1620 is generally between about 1 mm and about 2 mm.

The compact hearing aid 1600 also includes a recharging coil antenna 1616 disposed around the microphone 1608. The recharging coil antenna 1616 is used to recharge the first battery 1626 and the second battery 1628 daily. When positioned within the ear, the first battery 1626 and the second battery 1628 are disposed on opposite sides (i.e., the medial and lateral sides) of the tympanic membrane and the connecting member 1621 is disposed through the tympanic membrane.

Factors considered in the design of the various components, such as the actuator, of the compact hearing aids described herein are the amount of force to be applied to, and the amount of displacement of, the tympanic membrane to improve the user's hearing. The amount of force may vary based on the modulating mass or masses of between about 20 mg and about 30 mg, between about 0.05 microns and about 5.0 microns of displacement with a force of between about 0.001 Newtons (N) and about 0.05 N, across the audible frequency range.

Figure 17:
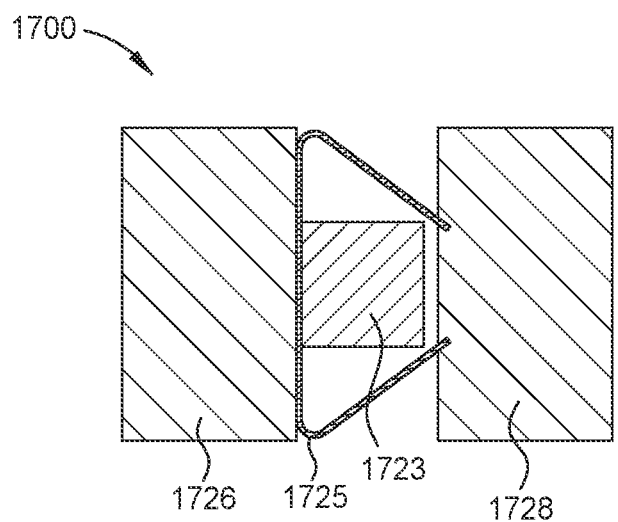
FIG. 17 depicts a schematic cross-sectional view of an actuation assembly of a compact hearing aid.
Figure 19:
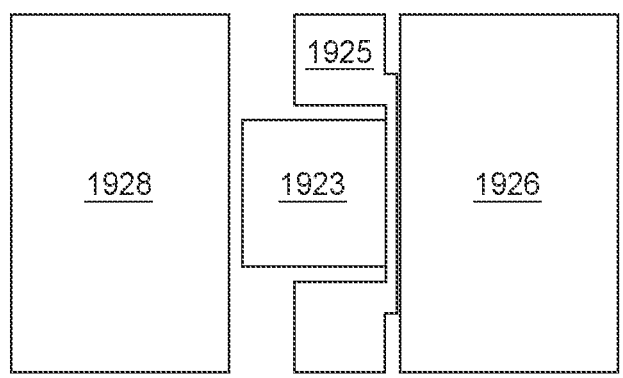
FIG. 19 depicts a schematic cross-sectional view of an actuation assembly of a compact hearing aid.
Figure 20:
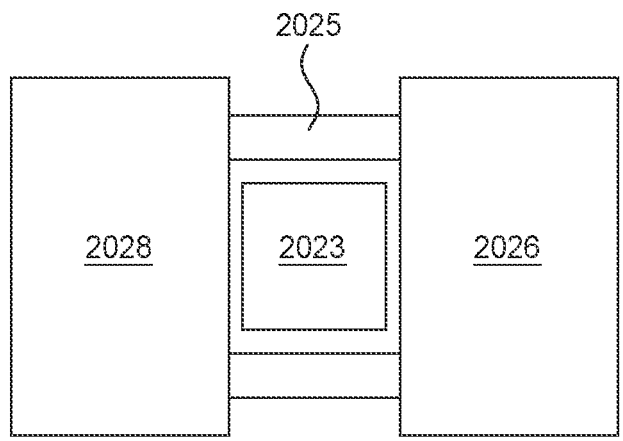
FIG. 20 depicts a schematic cross-sectional view of an actuation assembly of a compact hearing aid.

As shown in FIG. 17, the compact hearing aid includes an actuation assembly 1700, which may also include a displacement multiplier 1725 in conjunction with the actuator 1723 to amplify the actuation of the first mass, shown as a first battery 1726, as an example, and the second mass, shown as a second battery 1728, as an example. The displacement multiplier 1725 is shown as a piezo coupling arm lever, as an example. The arm lever displacement multiplier 1725 includes an actuator leg portion, a pivot on case portion, and a mass, shown as a battery, leg portion. . As shown in FIG. 19, the actuation assembly 1900 may also include a fixed coupling 1925 in conjunction with the actuator 1923. The fixed coupling 1925 is shown as a fixed coupling to the top of the actuator, as an example. As shown in FIG. 20, the actuation assembly 2000 may also include a rigid coupler 2025 in conjunction with the actuator 2023. The rigid coupler 2025 is shown as a rigid coupler between the first battery 2026 and the second battery 2028 and positioned around the outside of the actuator 2023, as an example.

Figure 21:
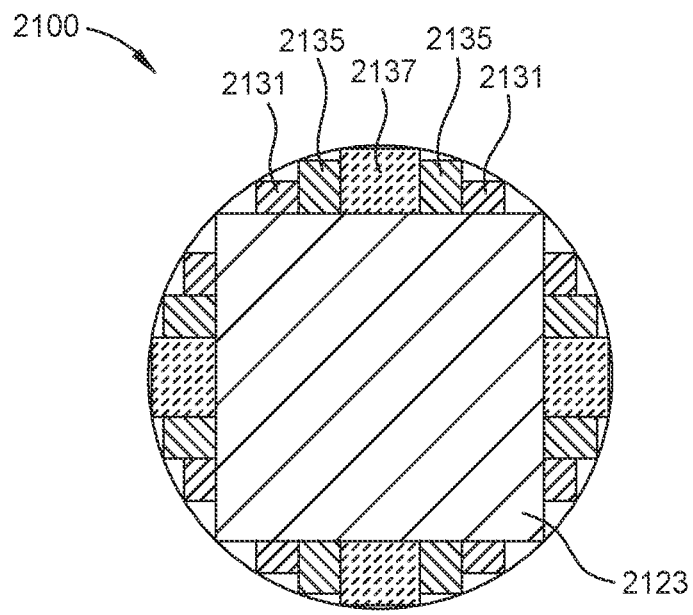
FIG. 21 depicts a top-down cross-sectional view of a portion of an actuation assembly of a compact hearing aid.
Figure 22:
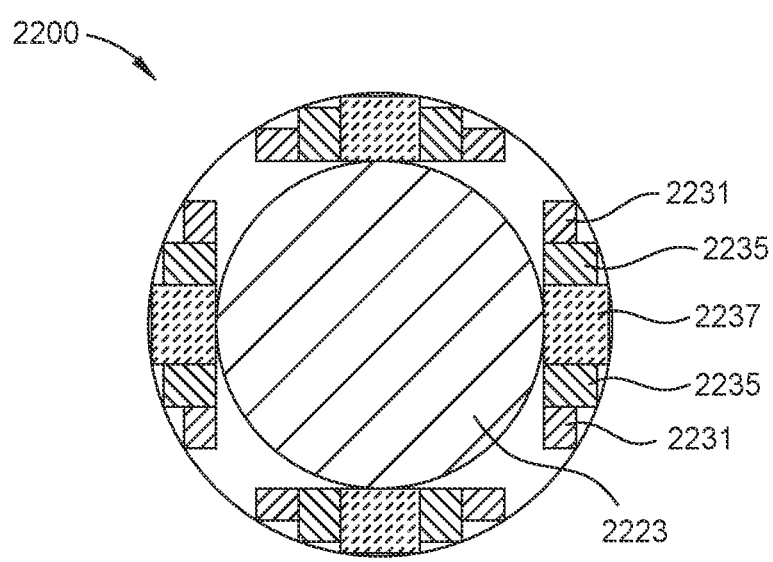
FIG. 22 depicts a top-down cross-sectional view of a portion of an actuation assembly of a compact hearing aid.

As shown in FIGS. 21 and 22, the various piezo couplings, including the arm lever displacement multiplier, the fixed coupling, and the rigid coupler, may include any suitable number of components surrounding or otherwise coupled to the actuator 2123 and 2223, respectively. The actuator 2123 is shown as a rectangular prism as an example, and the actuator 2223 is shown as a cylindrical tube as an example. The actuators 2123, 2223 are surrounded by a plurality of any suitable number and combination of rigid coupler portions 2131, 2231, fixed coupling portions 2135, 2235, and arm lever displacement multiplier portions 2137, 2237.

In addition to the aforementioned components, the disclosed compact hearing aids may also include additional components, such as sensors for detecting a change in the biological conditions of the ear, for example, infections, inflammation, scar tissue, or epithelial cell migration.

The housing 301 is generally any suitable covering which encloses and provides a sealed compartment for the device components. Suitable casings including, for example, biocompatible materials, such as silicon, fluoropolymers, polyethylene, stainless steel, and titanium. The housing 301 is either a solid or a porous material. In one embodiment, the housing 301 has micro holes to allow for venting. In another embodiment, the housing 301 is solid such that it does not have any venting holes therethrough. In another embodiment, the housing 301 is solid such that it does not have any venting holes therethrough and utilizes dead space to allow for compression created by internal movement. In some embodiments, the housing 301 includes linear channels to allow for internal pressure balancing due to internal movement of the actuator and mass (e.g., the battery). The linear channels also provide compensation for epithelial migration about the compact hearing aid 300. Even further, the linear channels provide mechanical benefits, such as improved stabilization.

Figure 18:
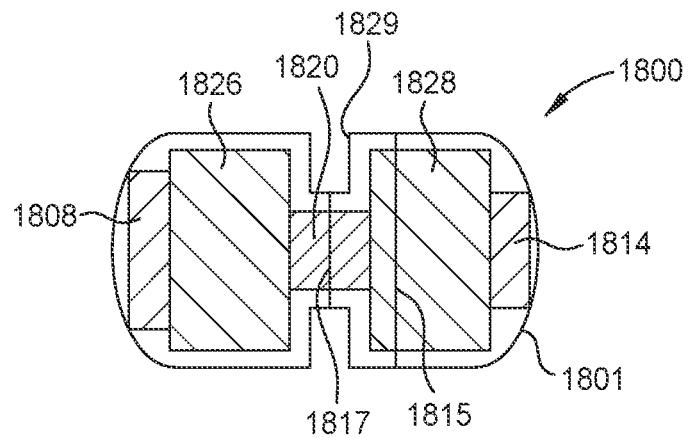
FIG. 18 depicts a schematic cross-sectional view of a compact hearing aid.

FIG. 18 depicts a schematic cross-sectional view of a compact hearing aid 1800. The compact hearing aid 1800 includes a housing 1801 which encloses a stack of components, which includes a microphone 1808, a processor 1814, a first portion 1826, shown as a first battery, a second portion 1828, shown as a second battery, and a connecting member 1820 having an actuator disposed therein.

The housing 1801 is between about 5 mm and about 10 mm in length, such as about 6 mm. The housing 1801 generally has two diameters, a first diameter 1815 and a second diameter 1817. The first diameter 1815, which generally corresponds to the flanged portions that rest on either side of the tympanic membrane, is between about 1 mm and about 5 mm, such as about 3 mm. The second diameter 1817, which corresponds to the portion of the compact hearing aid 1800 to be disposed through the tympanic membrane, is between about 0.5 mm and about 3 mm, such as about 1.5 mm. The notched portion 1829, in which the tympanic membrane is to be disposed is generally between about 0.15 mm and about 0.5 mm, such as about 0.25 mm, to provide sufficient space for the tympanic membrane without pinching the tympanic membrane such that it would cause necrosis.

Each of the microphone 1808 and the processor 1814 is between about 0.25 mm and about 1.0 mm thick, such as about 0.5 mm. Each of the first portion 1826, and the second portion 1828 is between about 1 mm and about 2 mm in height, such as about 1.5 mm, and has an outer diameter of between about 2 mm and about 3 mm, such as about 2.5 mm. The connecting member 1820, having an actuator disposed therein in some embodiments, or coupled thereto, is between about 0.5 mm and about 3 mm in height, such as about 1 mm, and has an outer diameter between about 0.5 mm and about 2 mm, such as about 1 mm. Similarly, in some embodiments, the actuator may be between about 0.5 mm and about 3 mm in height, such as about 1 mm, and have an outer diameter between about 0.5 mm and about 2 mm, such as about 1 mm.

As discussed above, the compact hearing aid can be of any suitable size and shape with components of various size and shape; however, each configuration generally requires the same various components, for example, the microphone, energy source, actuator, and processor.

Figure 7:
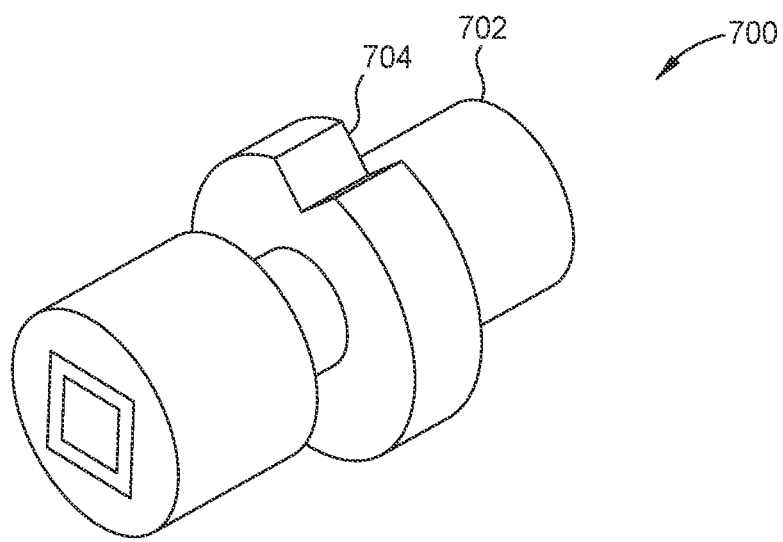
FIG. 7 is a schematic perspective view of an alternative embodiment of a compact hearing aid.

FIG. 7 is a schematic perspective view of an alternative embodiment of a compact hearing aid 700. As shown in FIG. 7, at least one flange 702, generally the medial flange, is interrupted by a pie-shaped notch 704 therein. The notch 704 is useful for insertion of the compact hearing aid 700 through the tympanic membrane because the notch 704 acts as an Archimedes screw, making it easier to fit the flange 702 through a smaller incision.

Figure 8:
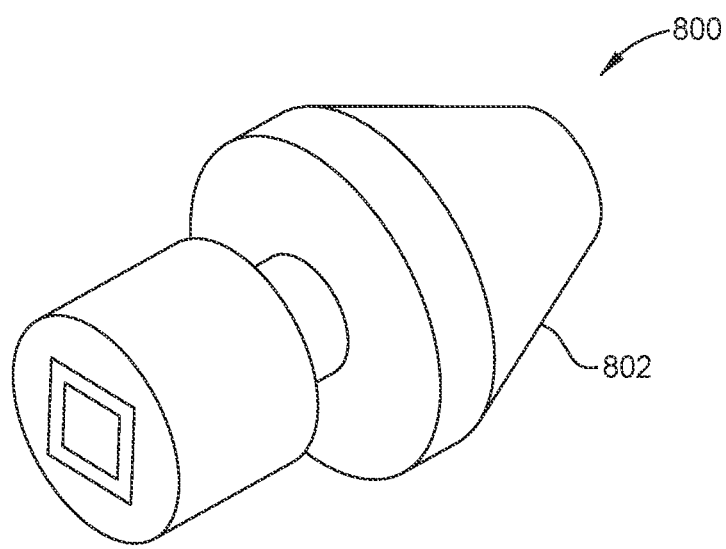
FIG. 8 is a schematic perspective view of an alternative embodiment of a compact hearing aid.

FIG. 8 is a schematic perspective view of an alternative embodiment of a compact hearing aid 800. The compact hearing aid 800 includes at least one flange 802, generally the medial flange, which is conical and acts as a dilator when inserted through an incision in the tympanic membrane.

In further embodiments, at least one of the first flange and the second flange of the compact hearing aid is otherwise tapered from a first end to a second end thereof, such that the first flange or the second flange acts as a dilator when inserted through an incision in the tympanic membrane.

Figure 9A:
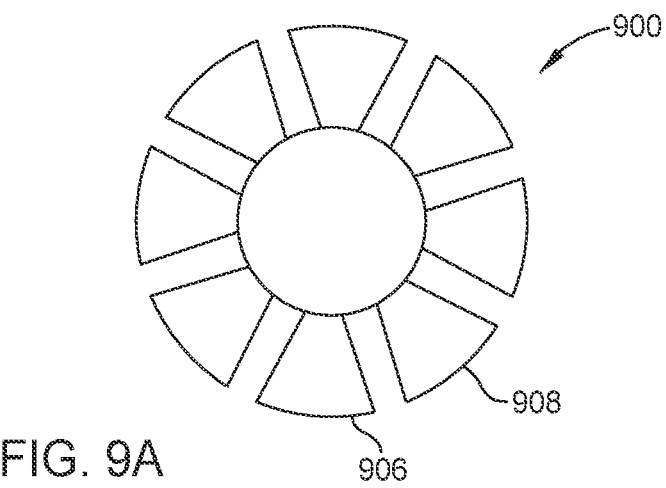
FIGS. 9A-9C depict an alternative embodiment of a compact hearing aid.
Figure 9B:
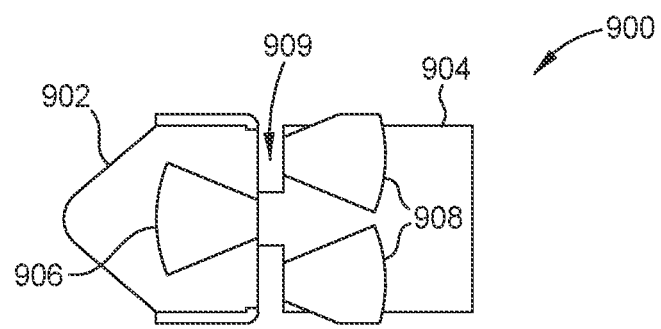
Figure 9C:
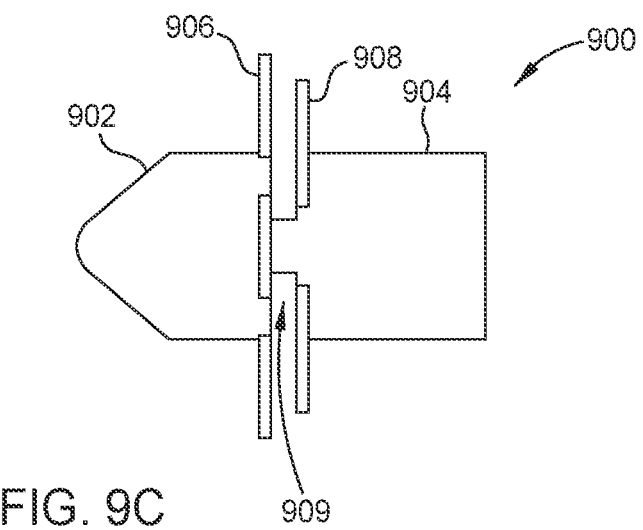

FIGS. 9A-9C depict various views of an alternative embodiment of a compact hearing aid 900. The compact hearing aid 900 includes a first flange 902 and a second flange 904. The first flange 902 has a plurality of first flange tabs 906 coupled thereto, and the second flange 904 has a plurality of second flange tabs 908 coupled thereto. The plurality of second flange tabs 908 are offset from the plurality of first flange tabs 906. As shown in FIG. 9B, and described further below, the first flange tabs 906 and the second flange tabs 908 generally lie flat against the compact hearing aid 900 until after the compact hearing aid 900 has been inserted through the tympanic membrane. After the compact hearing aid 900 is inserted, the plurality of first flange tabs 906 and/or the plurality of second flange tabs 908 are opened such that they lie parallel to the surface of the tympanic membrane to stabilize the compact hearing aid 900, as shown in FIG. 9C.

The mounting region of the disclosed compact hearing aids generally includes one or more flanges, such as the first flange 902 and the second flange 904, which are positioned to optimize energy transfer to the tympanic membrane, with a space 909 therebetween configured for the tympanic membrane to be disposed therein. The mounting region provides for retention of the compact hearing aid, such as compact hearing aid 900, in the tympanic membrane. In addition, the mounting region provides for balance and stabilization of the compact hearing aid 900 in the tympanic membrane. In further embodiments, the one or more flanges may deliver actuation or modulation to the tympanic membrane. In some embodiments, the one or more flanges contain a charging coil or charging array. In addition, in some embodiments, the one or more flanges include predesigned features to provide offset forces to avoid pinching or clamping of the tympanic membrane since such pinching or clamping often causes necrosis of, or a hole in, the tympanic membrane.

In further embodiments, at least one of the first flange and the second flange is compressible and can be deployed or released into its final shape or position once inserted through the tympanic membrane.

The above-described embodiments provide exemplary shapes and configurations of the one or more flanges. However, the present disclosure contemplates further shapes and configurations, including but not limited to, circular flanges resembling a top hat, circular flanges resembling a top hat having a brim turned up about the outer edge, a skirt that flairs away from the body that curls up around its edges, a circular flange that is undercut on the side that faces the tympanic membrane, while the outer ring is turned upward distributing the clamping force to the outer rim of the flange, and a flange that is created by a micro-wire form that is covered by a thin film of material or polymer and can also be used as the recharging coil for inductive recharging. In some embodiments, the surface of the brim may a multi-plane surface, such as a wavy surface or a stepped surface.

In some embodiments, the flanges which stabilize the compact hearing aid are juxtaposed across the tympanic membrane to avoid opposing pressure maintaining vascular profusion about the tympanic membrane and avoiding necrosis. Such flanges generally include tabs arranged around the circumference of the flange that individually flare away from the flange and body of the compact hearing aid. The tabs can be various shapes, including but not limited to, pie shaped, lobes, dual lobes, or clover shaped.

In yet another embodiment, the mounting region includes an array of intermittent flanges that is undercut on the side that faces the tympanic membrane, while the outer edge of the intermittent flanges may be turned upward to distribute the force to the outer rim of the flange. The array can be placed on the medial and lateral sides to sandwich the tympanic membrane therebetween, or offset radially to ensure the tympanic membrane is not pinched between stabilizing flanges.

In further embodiments, the flanges are designed to stabilize the compact hearing aid and are positioned to, or have features to, mitigate the challenges of epithelial migration on the lateral side of the tympanic membrane. The flanges can be juxtaposed with retention and stabilizing features on the medial side. Suitable features include, but are not limited to, bump patterning, bi-lateral hatching, linear tracks or channels, axial tracks, patterning of tear drop shaped raised portions, and boat hull-shaped configurations. In still further embodiments, these features may additionally or alternatively be patterned on other portions of the disclosed compact hearing aids, such as the body.

In still further embodiments, at least one of the one or more flanges includes an actuator component, which extends from the compact hearing aid to modulate the malleus or umbo directly. In still further embodiments, an actuator may extend from other portions of the compact hearing aid, such as the body, to modulate the malleus or umbo directly.

The flanges disclosed herein, alone or in any combination, may interact with the body of the compact hearing aid and/or with the tympanic membrane in any suitable manner.

Methods of Implantation

Figure 10:
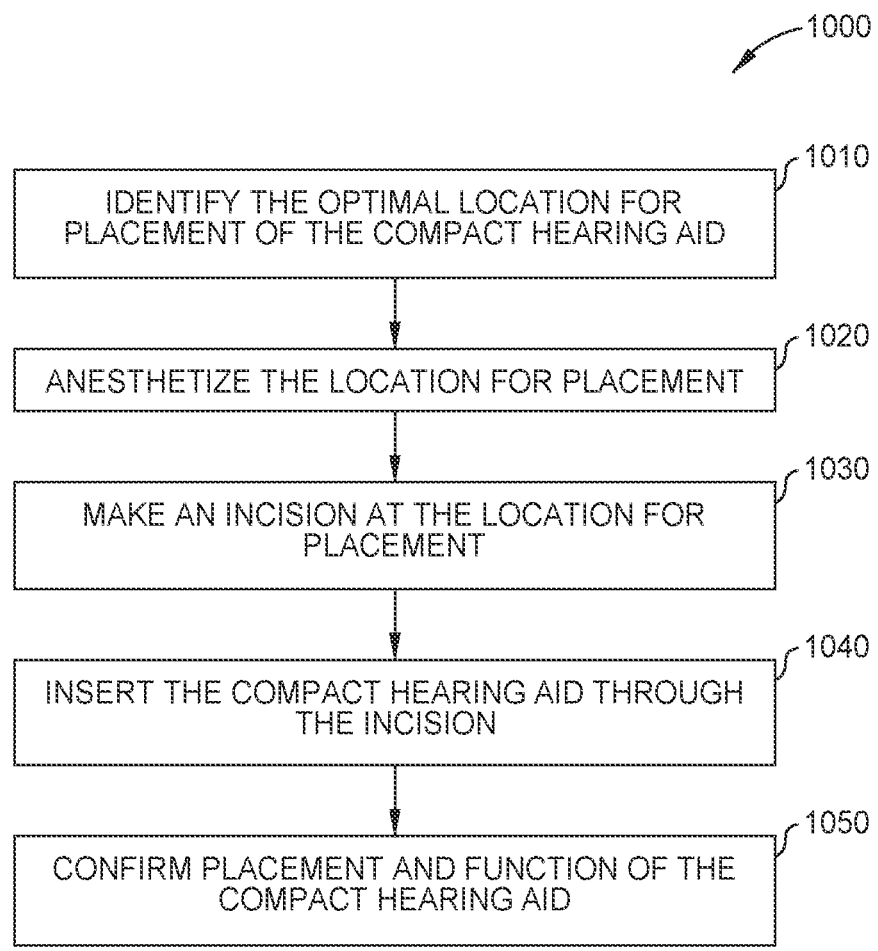
FIG. 10 is a process flow of a method for inserting a compact hearing aid.

The disclosed compact hearing aids are implantable by any suitable implantation method. FIG. 10 is a process flow of one such method 1000.

Prior to the method 1000, an optional cleaning may be performed to clean the tympanic membrane and the proximal external auditory canal.

The method 1000 generally includes identifying the optimal location for placement of the compact hearing aid at operation 1010, anesthetizing the location for placement at operation 1020, making an incision, or any other puncture, at the location for placement at operation 1030, and inserting the compact hearing aid through the incision at operation 1040. The method 1000 generally further includes confirming the placement and the functionality of the compact hearing aid at operation 1050.

In one embodiment, the optimal location is the anterior inferior quadrant of the tympanic membrane. Accordingly, the method includes anesthetizing a portion of the anterior inferior quadrant, making a small incision, such as less than or equal to about 2 mm, for example less than or equal to about 1 mm, and inserting the compact hearing aid through the incision to position the compact hearing aid in the user's anterior inferior quadrant of the tympanic membrane.

As discussed above, some embodiments of the compact hearing aids include configurations that are adapted for easier insertion through the tympanic membrane. For example, at least one of the one or more flanges may include a slotted or interrupted flange, such as the compact hearing aid 700 shown in FIG. 7, to aid in placement across an incision in the tympanic membrane by rotating the compact hearing aid through the incision.

In another embodiment, such as the compact hearing aid 800 of FIG. 8, at least one of the one or more flanges, such as the medial flange, or the body of the compact hearing aid itself, is conically-shaped such that it serves as a dilator, which provides a profile to be pushed through the incision in the tympanic membrane to dilate the incision and allow the medial portion of the compact hearing aid to pass therethrough.

In yet another embodiment, at least one of the medial and lateral flange is a self-expanding flange that is insertable through the incision and expandable in the middle ear such that it will lie against the medial side of the tympanic membrane once expanded. In still further embodiments, the distance between the flanges, or intermittent portions thereof, is predetermined to allow for implantation and for providing adjustment for variable thickness of the tympanic membrane and/or variable force.

In even further embodiments, the compact hearing aid includes multiple pieces, which can be coupled together to form the entire compact hearing aid. In such embodiments, the medial and lateral flanges are generally connected by an array of connectors that are fixed in one or both halves and that couple to corresponding receptacles on one or both halves. After one piece of the compact hearing aid is inserted through the incision, for example through the tympanic membrane, then the second piece is coupled to the already inserted piece, for example, by piercing the tympanic membrane with the array of pins that mate with the already inserted piece. In still further embodiments, one piece is inserted through the incision to the medial side of the tympanic membrane and a second piece is coupled to the first piece across the tympanic membrane at a location a distance away from the initial placement incision. In such embodiments, the initial placement incision will heal up.

Methods of Removal for Emergency or Safety Reasons

The disclosed compact hearing aids can be quickly and safely removed for safety and emergency reasons. For example, as discussed above, embodiments of the compact hearing aids are configured to turn off upon recognition of a particular audio signature frequency. If the particular audio signature fails to turn off the compact hearing aid, or if the compact hearing aid needs to be removed for emergency reasons, then the device may be inactivated and/or removed by physical means.

In one embodiment, the lateral flange of the disclosed compact hearing aids includes a switch, a pressure switch, a contact point, a slide, or any combinations thereof. A medical professional may contact the switch, the pressure switch, the contact point, the slide, or the combinations thereof using basic medical tools in an emergency room or other medical setting to inactivate the compact hearing aid after the compact hearing aids fails to turn off in response to the audio signature frequency. In some embodiments, the lateral flange of the disclosed compact hearing aids incorporates a feature to assist in the removal of the compact hearing aid that can be grasped or connected with general medical tools such as tweezers, probes, and forceps.

In still further embodiments, users of the disclosed compact hearing aids are provided with a custom configured inactivation or retrieval tool that can be used by a medical professional to remove or inactivate the device in emergency situations.

Devices for Implantation and Retrieval

The disclosed compact hearing aids can be implanted into a patient's ear during a minimally-invasive, outpatient procedure. In one embodiment, the disclosed compact hearing aids are inserted using a scalpel, or any suitable cutting instrument, to create a small incision, or any other puncture, and a tool is used to hold the compact hearing aid and position the contact hearing aid through the tympanic membrane. In another embodiment, an implantation tool, which generally includes an elongate rod having a cutting tool on a distal end thereof, is inserted through the ear canal to the appropriate position on the tympanic membrane. The cutting tool positions the compact hearing aid at the location for placement using a distal alignment ring guide, advances a cutting instrument, such as a blade or a needle, of a predetermined, suitable size to create an incision at the location for placement, and then advances the compact hearing aid across the tympanic membrane to dispose the compact hearing aid therethrough.

Figure 11A:
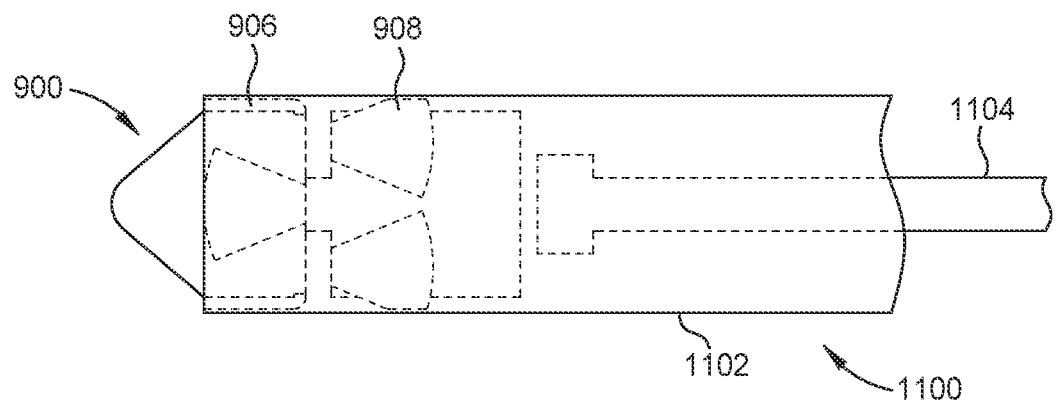
FIGS. 11A-11B depict the compact hearing aid of FIGS. 9A-9C with a portion of an implantation tool at various stages of implantation.
Figure 11B:
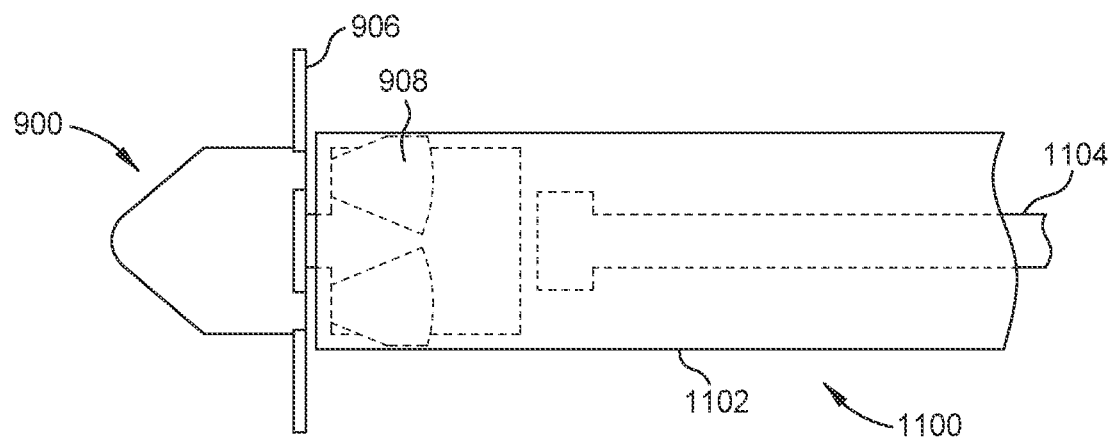

The configuration of the device for implantation and retrieval may be varied to more easily insert specific configurations of the disclosed compact hearing aids. For example, FIGS. 11A-11B depict the compact hearing aid 900 of FIGS. 9A-9C with a portion of an exemplary implantation tool. As shown in FIGS. 11A-11B, the implantation tool 1100 includes a sheath 1102 and an advancement rod 1104. In operation, the sheath surrounds the compact hearing aid 900 and keeps the plurality of first flange tabs 906 and the plurality of second flange tabs 908 in their non-expanded position such that they lie flat alongside the compact hearing aid 900, as shown in FIG. 11A.

A portion of the sheath 1102 is generally inserted through the incision made in the tympanic membrane and once the sheath 1102 has been inserted through the tympanic membrane, then at least a portion of the sheath 1102 is withdrawn. The compact hearing aid 900 is thus disposed through the tympanic membrane, such that a first portion of the compact hearing aid 900 is disposed on the medial side of the tympanic membrane and a second portion of the compact hearing aid 900 is disposed on the lateral side of the tympanic membrane. Once the portion of the compact hearing aid 900 having the plurality of first flange tabs 906 is released from the sheath 1102, the advancement rod 1104 maintains its position while the sheath 1102 is withdrawn. The first flange tabs 906 expand, flare out, or otherwise deploy, and form a flange alongside the tympanic membrane, as shown in FIG. 11B.

In another embodiment, one or more tools, such as cupped forceps, are inserted through a primary opening for accessing the medial side of tympanic membrane, thereupon the two or more components are joined across the tympanic membrane through various mechanisms, such as pins or snaps. The one or more tools, such as the cupped forceps are then removed.

Figure 15A:
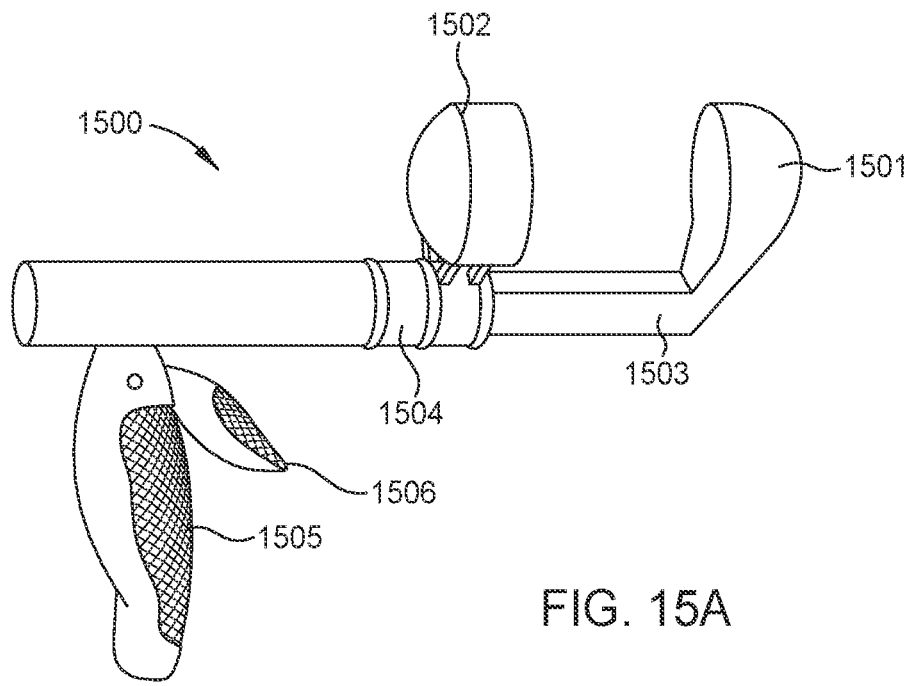
FIGS. 15A-15B depict an alternative embodiment of an implantation tool.
Figure 15B:
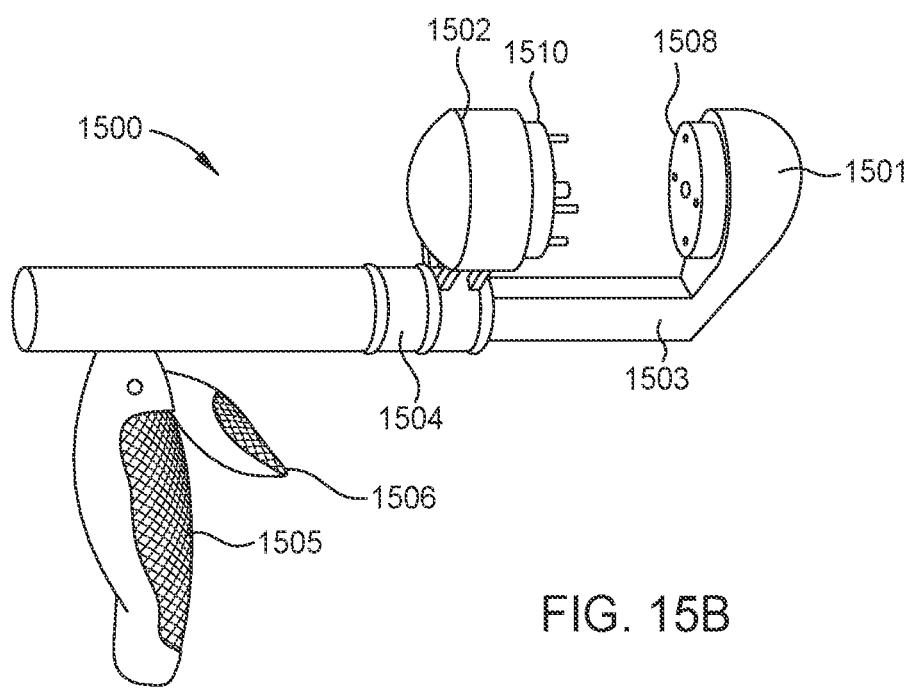

FIGS. 15A-15B depict an alternative embodiment of an implantation tool 1500. The implantation tool 1500 includes a distal cup 1501, a proximal cup 1502, a connecting member 1503, an advancing member 1504, a handle 1505 and an actuating trigger 1506. The implantation tool 1500 is configured to hold one or more devices to be implanted.

The operation of the implantation tool 1500 will be described in the context of inserting a compact hearing aid through the tympanic membrane. However, it is contemplated that the implantation tool 1500 is useful to implant any suitable device in any suitable location throughout the body.

As shown in FIG. 15B, the implantation tool is configured to hold a first portion 1508 and a second portion 1510 of a compact hearing aid, such as the compact hearing aids disclosed herein.

In operation, the distal cup 1501 holding the first portion 1508 is advanced through an incision in the tympanic membrane such that the distal cup 1501 and the first portion 1508 are disposed on the medial side of the tympanic membrane while the proximal cup 1502 and the second portion 1510 are disposed on the lateral side of the tympanic membrane. The actuating trigger 1506 can then be used to actuate the distal cup 1501 and/or the proximal cup 1502 to snap the first portion 1508 and the second portion 1510 of the compact hearing aid together through the tympanic membrane at a distance away from the incision. Once the compact hearing aid has been snapped together and implanted through the tympanic membrane, the implantation tool 1500 is withdrawn through the incision and the hearing aid is left in place through the tympanic membrane.

Devices and Systems for Recharging

The present disclosure further contemplates recharger devices and systems for providing a user interface to recharge the implanted compact hearing aids easily. The recharger devices and systems interact with the charging circuitry to recharge the disclosed compact hearing aids. The recharger devices and systems are generally disposed in the ear canal, over the ear, around the ear, or in the vicinity of the user's head. Exemplary rechargers include ear buds, inner ear canal inserts, ear muffs, over-the-ear clips, glasses stem clips, devices in or around a pillow, and devices in or around the vicinity of the user's head, that can be placed in the ear canal, over the ear, around the ear, or in the vicinity of the user's head to interact with the recharging circuit. In some cases, the recharger device itself will need to be recharged. In one embodiment, the recharging system is a cradle system that provides a support cradle for the recharge device, which is coupled to a power source such as, an outlet, a USB port, or an automobile power source. In another embodiment, the recharge device itself may be directly connected to a power source through a connector, such as prongs. It is also contemplated that the recharging system can be modular such that a head set would provide holders for the ear components and hold them in place while they are being worn by the patient and additional holders for holding them while they are recharging. The charging components that are placed in the ear canal can be disconnected from the head set system to be more discreet and to allow for mobile recharging.

Docking Devices

The present disclosure also contemplates docking devices for docking one or more devices in a user's ear, such as through the tympanic membrane. Like embodiments of the compact hearing aids described herein, the docking devices may also include any suitable configurations of a first flange and a second flange connected by a connecting member. However, the docking devices generally do not include the components of the hearing aid described above. Instead, the docking devices generally include a hollow portion therethrough, which is predesigned to dock another device therein. Much like the disclosed compact hearing aids, the docking devices can be inserted during a minimally-invasive outpatient procedure. The procedure generally includes identifying the optimal location for placement of the docking device, anesthetizing the location for placement, making an incision, or any other puncture, at the location for placement, and inserting the docking device through the incision. The procedure may also include cleaning the location for placement, as well as confirming the placement and the functionality of the docking device after the docking device has been placed.

Suitable devices to be docked include, but are not limited to, biometric devices, diagnostic instruments, entertainment modules, covert communication modules, therapeutic devices, fitness tracking devices, health tracking devices, tissue stimulating devices, and assistive hearing devices. These docking devices beneficially provide a docking station in the ear, such as through the tympanic membrane, which allows for various devices to be placed therein over time. Since the docking device has already been placed at the predetermined location for placement, an additional incision does not need to be made at the placement location when the device is docked in the docking device.

Stimulating and/or Modulating Devices

While the present disclosure discusses the disclosed devices being used as compact hearing aids. The present disclosure also contemplates stimulating and/or modulating devices, which are positionable, for example, in any tissue throughout the user's body. Such tissue stimulating devices similarly include a housing with various components therein, such as one or more sensors, one or more masses, one or more energy sources, which may be used as the one or more masses, one or more processors, and one or more actuators. The one or more sensors are generally any suitable sensors to provide a predetermined output, the predetermined output being based on the desired effect on the user's body. Exemplary output includes, but is not limited to, mechanical, electrical, and thermal output. In operation, the stimulating and/or modulating devices are useful to effect change on a number of different tissues in the body, such as muscles, ligaments, membranes, bones, and cartilage.

Conclusion

Embodiments of the present disclosure provide improved compact hearing aids that use vibration transduction to directly or indirectly modulate the velocity or the position of the tympanic membrane. This direct or indirect modulation of the velocity or the position of the tympanic membrane significantly improves sound quality for the user. The disclosed compact hearing aids are more compact, more comfortable, and less cosmetically noticeable. Indeed, since the disclosed compact hearing aids may be disposed in the ear canal and across the tympanic membrane, the disclosed compact hearing aids are invisible from the outside observer. In addition, because of the compact design of the disclosed compact hearing aids, the compact hearing aids do not totally block the ear canal. Instead, the disclosed compact hearing aids leave the ear canal unobstructed and thus provide a more natural and improved sound quality for the user. Additionally, the disclosed compact hearing aids provide additional functionality, such as avoiding the canal occlusion effect and hearing aid feedback associated with conventional hearing aids. Moreover, the disclosed compact hearing aids can be inserted and removed during a minimally-invasive outpatient procedure.

While the foregoing is directed to embodiments of the present disclosure, other and further embodiments of the disclosure may be devised without departing from the basic scope thereof, and the scope thereof is determined by the claims that follow.

What is claimed is:

1. A hearing aid for insertion through a patient's tympanic membrane, the hearing aid comprising:
   a housing, comprising:
      a first portion configured to be disposed on one of a medial side or a lateral side of the patient's tympanic membrane;
      a second portion configured to be disposed on a side of the patient's tympanic membrane opposite from the first portion; and
      a connecting portion disposed between the first portion and the second portion and configured to be disposed through the patient's tympanic membrane;
   an actuation mass, comprising:

a first mass structure enclosed within the first portion of the housing; and a second mass structure enclosed within the second portion of the housing and coupled to the first mass structure via a connecting member disposed through the connecting portion of the housing; and at least one actuator coupled to the actuation mass and enclosed within at least one of the first portion and the second portion of the housing or through the connecting portion of the housing, the actuator configured to convert electrical signals into mechanical motion to actuate the actuation mass and modulate the patient's tympanic membrane.

2. The hearing aid of claim 1, wherein the at least one actuator comprises a piezoelectric actuator.

3. The hearing aid of claim 2, wherein the piezoelectric actuator comprises a piezoelectric film stack.

4. The hearing aid of claim 2, wherein the piezoelectric actuator comprises a piezoelectric microtube.

5. The hearing aid of claim 1, wherein the at least one actuator comprises a micro-electro-mechanical systems (MEMS) actuator.

6. The hearing aid of claim 1, wherein the at least one actuator comprises a piezo MEMS actuator.

7. The hearing aid of claim 1, wherein the at least one actuator comprises a voice coil actuator.

8. The hearing aid of claim 1, wherein the at least one actuator is disposed within the connecting member between the first mass structure and the second mass structure.

9. The hearing aid of claim 1, wherein the actuation mass comprises an energy source.

10. The hearing aid of claim 9, wherein the energy source comprises a thin film battery, a radio thermal generator, a super capacitor, a thick film battery, or a lithium (Li) ion battery.

11. A hearing aid for insertion through a patient's tympanic membrane, the hearing aid comprising:
a housing, comprising:
a first portion configured to be disposed on one of a medial side or a lateral side of the patient's tympanic membrane;
a second portion configured to be disposed on a side of the patient's tympanic membrane opposite from the first portion; and
a connecting portion coupling the first portion and the second portion and configured to be disposed through the patient's tympanic membrane;
at least one mass, comprising:
a first mass structure enclosed within the first portion of the housing; and
a second mass structure enclosed within the second portion of the housing; and
at least one actuator coupled to the at least one mass.

12. The hearing aid of claim 11, further comprising:
a microphone; and
a processor in communication with the microphone and enclosed within the first portion or the second portion of the housing.

13. The hearing aid of claim 12, wherein the microphone comprises a piezo MEMS microphone or an electrostatic microphone.

14. The hearing aid of claim 11, wherein the at least one mass comprises an energy source for the at least one actuator.

15. The hearing aid of claim 14, further comprising:
a recharging circuit enclosed within the first portion or the second portion of the housing for recharging the energy source.

16. The hearing aid of claim 11, wherein the second mass structure is coupled to the first mass structure via a connecting member.

17. The hearing aid of claim 16, wherein the first mass structure comprises a battery and the second mass structure comprises an inactive counter mass.

18. A hearing aid for insertion through a patient's tympanic membrane, the hearing aid comprising:
a housing, comprising:
a first flange portion;
a second flange portion; and
a connecting portion disposed between the first flange portion and the second flange portion;
at least one mass enclosed within at least the first flange portion and the second flange portion; and
an actuator coupled to the at least one mass.

19. The hearing aid of claim 18, wherein the at least one mass comprises:
a first mass structure disposed within the first flange portion;
a second mass structure disposed within the second flange portion; and
a connecting member coupling the first mass structure and the second mass structure through the connecting portion of the housing.

20. The hearing aid of claim 19, wherein the at least one mass has a dumbbell morphology.

* * * * *